United States Patent [19]
Kamijo et al.

[11] Patent Number: 5,188,833
[45] Date of Patent: Feb. 23, 1993

[54] FREEZE-DRIED PHARMACEUTICAL PREPARATIONS FOR PARENTERAL USE

[75] Inventors: Shinji Kamijo, Tokyo; Jun Imai, Kanagawa; Hiromichi Kodaira, Tochigi, all of Japan

[73] Assignee: Kyorin Seiyaku Kabushiki Kaisha, Tokyo, Japan

[21] Appl. No.: 644,686

[22] Filed: Jan. 22, 1991

Related U.S. Application Data

[63] Continuation of Ser. No. 291,244, Dec. 28, 1988, abandoned.

[30] Foreign Application Priority Data

Dec. 28, 1987 [JP] Japan .................... 62-334923

[51] Int. Cl.$^5$ .................. A01N 25/02; A01N 43/54; A61K 31/505
[52] U.S. Cl. .................. 424/405; 424/422; 424/423; 514/257; 514/267
[58] Field of Search .............. 514/257, 267; 424/422, 424/423, 405

[56] References Cited

U.S. PATENT DOCUMENTS 4,839,355  6/1989  Lesher .................. 514/224.5

FOREIGN PATENT DOCUMENTS 0067666  12/1982  European Pat. Off.

Primary Examiner—Thurman K. Page
Assistant Examiner—C. Azpuru
Attorney, Agent, or Firm—McAulay, Fisher, Nissen, Goldberg & Kiel

[57] ABSTRACT

Freeze-dried pharmaceutical preparation containing antibacterial quinolinecarboxylic acid derivatives are provided. These preparations are characterized by their stability against light and heat and have rapid solubility.

13 Claims, No Drawings

FREEZE-DRIED PHARMACEUTICAL PREPARATIONS FOR PARENTERAL USE

This is a continuation of application Ser. No. 291,244, filed Dec. 28, 1988, now abandoned.

BACKGROUND OF THE INVENTION

I. Field of the Invention

This invention relates to freeze-dried pharmaceutical preparations containing antibacterial quinolinecarboxylic acid derivatives which preparations exhibit excellent stability against light and heat and rapid splubility.

II. Description of the Prior Art

In this invention, the antibacterial quinoline-carboxylic acid derivatives have the following general formula (I),

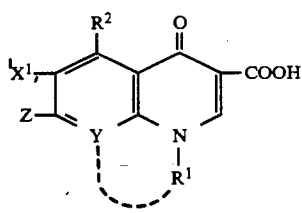

wherein $R^1$ represents a cycloalkyl group having 3 to 6 carbon atoms, straight or branched lower alkyl group, lower haloalkyl group, lower alkenyl group, lower hydroxyalkyl group, lower alkylamino group or substituted or unsubstituted phenyl groupl; $R^2$ represents a hydrogen atom, halogen atom, nitro group or amino group; $X^1$ represents a halogen atom; Y represents a nitrogen atom or $CX^2$, (wherein $X^2$ represents a hydrogen atom, halogen atom, lower alkyl or alkoxy group, or $X^2$ and $R^1$ together are atom, lower alkyl alkoxy group, or $X^2$ and $R^1$ together are $-O-CH_2CH(CH_3)-$, $-CH_2CH_2CH(CH_3)-$, $-CH_2CH(CH_3)-$), Z represents

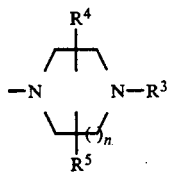

wherein n is 1 or 2. $R^3$ represents a hydrogen atom or lower alkyl group, $R^4$ and $R^5$ each represent independently a hydrogen atom, lower alkyl group, lower aminoalkyl group, lower hydroxyalkyl group or phenyl group or

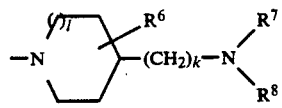

wherein k is 0 or 1, l is 0, 1 or 2, $R^6$ represents a hydrogen atom, halogen atom, lower alkyl group or hydroxy group, $R^7$ represents a hydrogen atom, lower alkyl group, lower haloalkyl group or lower hydroxyalkyl group, $R^8$ represents a hydrogen atom or lower alkyl group; the hydrates or the pharmaceutically acceptable acid addition or alkali salts thereof. (As used herein, "lower" when used in connection with alkyl or alkenyl means having 1 to 3 carbon atoms.)

It is known that most of these compounds have relatively low solubility in water. There have been a variety of studies to improve the solubility. For instance, a solution of antibacterial quinolinecarboxylic derivatives could be prepared by adding lactic acid or the like (Japanese Laid-Open Patent Application Sho 60-94910 which corresponds to EP-A-0 138 018) or alkali (Japanese Laid-Open Patent Application Sho 61-180771 which corresponds to EP-A-0 187 315).

However, even after the dissolution of the compounds in water was achieved, it was difficult to develop a stable pharmaceutical solution satisfactory for parenteral use, because the solution easily discolored under exposure to light or by heating and formed some decomposed materials. Therefore, a pharmaceutical solution containing antibacterial quinolinecarboxylic acid derivative suitable for parenteral use has not been achieved by these procedures.

SUMMARY OF THE INVENTION

The present inventors have discovered freeze-dried pharmaceutical preparations containing antibacterial quinoline-carboxylic acid derivatives of formula I which are extremely stable against either light or heat, have good solubility in water, retain their antibacterial activity, and are suitable for parenteral use. The freeze-dried pharmaceutical preparations of the present invention can be prepared by dissolving the quinolinecarboxylic acid derivatives, by adding acid, alkali and/or water, immediately followed by refrigeration under $-40°$ C. The solution is then freeze-dried under a vacuum to give a fine cake of the soluble, stable preparation.

DESCRIPTION OF THE PREFERRED EMBODIMENT

The acid is preferably lactic acid, acetic acid or hydrochloric acid, and the alkali is preferably sodium hydroxide or potassium hydroxide. The concentration of quinolinecarboxylic acid derivative in the solution to be refrigerated may be within a range from 0.1 to 30 w/v %, preferably from 5 to 15 w/v %. If the concentration is less than 0.1 w/v %, the volume of the solution becomes too large and a large vessel or a large injector will be required, which is inconvenient. On the other hand, if the concentration is higher than 30 w/v %, freeze-drying becomes difficult since the solution cannot be frozen easily by refrigeration.

The solution may be sterilized by filtration through a membrane filter (pore size 0.22 μm) and then be filled into vials. The solution in the vials is cooled to below $-40°$ C. As a general procedure, the vials are directly cooled by contacting with a refrigerant so as to obtain a rapid cooling. The cooling condition can be selected according to the ability of refrigerant and/or refrigerator, but no limitation is needed with respect to the cooling condition. Whatever condition to refrigerate the solution to below $-40°$ C. is applicable.

The freeze-drying can be performed according to conventional procedures and conditions under a vacuum using vacuum pump and mild elevation of temperature. As for the freeze-drying method, the conventional heat shock method or a method characterized by adding a solvent can also be used. After drying is completed, the vials are sealed, for example, with rubber stopper.

Medically usable adjuvants may be added to the freeze-dried pharmaceutical preparations of the present invention, such as excipients, adjuvants to provide isotonicity, pH adjusters, stabilizers, solubilizers, buffering agents and preservatives. The excipients or adjuvants providing isotonicity may be xylitol, D-sorbitol, D-mannitol, fructose, glucose, sucrose, lactose, gelatin, and the like. The pH adjuster may also be lactic acid, acetic acid, hydrochloric acid, sodium hydroxide or potassium hydroxide.

The following examples illustrate the present invention, but are not intended to limit its scope.

In the following examples, the quinolinecarboxylic acid derivatives used are 6,8-difluoro-1-(2-fluoroethyl)-1,4-dihydro-7-(4-methyl-1-piperazinyl)-4-oxo-3-quinolinecarboxylic acid (hereinafter referred to as AM-833), 1-ethyl-6-fluoro-1,4-dihydro-4-oxo-7-(1-piperazinyl)-3-quinolinecarboxylic acid (hereinafter referred to as NFLX), 9-fluoro-2,3-dihydro-3-methyl-10-(4-methyl-1-piperazinyl)-7-oxo-7H-pyrido[1,2,-3de][1,4]-benzoxazine-6-carboxylic acid (hereinafter referred to as OFLX), 1-cyclopropyl-6-fluoro-1,4-dihydro-4-oxo-7-(1-piperazinyl)-3-quinolinecarboxylic acid (hereinafter referred to as CPFX), 1-ethyl-6-fluoro-1,4-dihydro-4-oxo-7-(1-piperazinyl)-1,8-naphthyridine-3-carboxylic acid (hereinafter referred to as ENX), 7-(3-amino-1-pyrrolidinyl)-8-chloro-1-cyclopropyl-6-fluoro-1,4-dihydro-4-oxo-3-quinolinecarboxylic acid (hereinafter referred to as AM-1091), 1-ethyl-6,8-difluoro-1,4-dihydro-7-(3-methyl-1-piperazinyl)-4-oxo-3-quinolinecarboxylic acid (hereinafter referred to as NY-198), 7-(3-amino-1-pyrrolidinyl)-1-(2,4-difluorophenyl)-6-fluoro-1,4-dihydro-4-oxo-1,8-naphthyridine-3-carboxylic acid p-toluene-sulfonic acid hydrate (hereinafter referred to as T-3262).

EXAMPLE 1

Ten grams of powdered AM-833 were dissolved in 50 ml of 1M lactic acid, the pH was adjusted to 4.5 with 1N sodium hydroxide solution, and diluted with distilled water for injection to 100 ml. This solution was filtered through a membrane filter (pore size 0.22 µm) and each 2 ml of the filtrate was filled into clean and sterilized vials. These vials were cooled to −42° C., and dried under vacuum. The temperature of the shelf was kept at −20° C. during the initial stage (up to 22 hours) of drying. Under vacuum, the temperature was elevated to 20° C. and kept for 24 hours, and it was further elevated to 40° C. and kept for 6 hours to give a freeze-dried pharmaceutical preparation containing AM-833.

EXAMPLE 2

Fifteen grams of powdered AM-833 were dissolved in 75 ml of 1M lactic acid, the pH was adjusted to 4.0 with 1N sodium hydroxide solution, and diluted with distilled water for injection to 100 ml. This solution was filtered through a membrane filter (pore size 0.22 µm), and each 1.33 ml of the filtrate was filled into clean and sterilized vials. These vials were cooled to −40° C. and dried under vacuum in a manner similar to that of Example 1 to give a freeze-dried pharmaceutical preparation containing AM-833.

EXAMPLE 3

Ten grams of powdered AM-833 and 10 grams of glucose were dissolved in 50 ml of 1M lactic acid, the pH was adjusted to 4.5 with 1N sodium hydroxide solution, and diluted with distilled water for injection to 100 ml. This solution was filtered through a membrane filter (pore size 0.22 µm), and each 2 ml of the filtrate was filled into clean and sterilized vials. These vials were cooled to −40° C. The temperature was elevated to −10° C., and kept for 5 hours. Then, it was lowered again to −40° C. and dried under vacuum. The temperature of the vials was kept at −20° C. during the initial stage (up to 66 hours) of drying. Under vacuum, the temperature was elevated to 20° C. and kept for 5 hours to give a freeze-dried pharmaceutical preparation containing AM-833.

EXAMPLE 4

Ten grams of powdered AM-833 were dissolved in 55 ml of 1N sodium hydroxide solution, and the pH was adjusted to 10.1 with 1M lactic acid, and diluted with distilled water for injection to 100 ml. This solution was filtered through a membrane filter (pore size 0.22 µm), and each 2 ml of the filtrate was filled into clean and sterilized vials. These vials were cooled to −44° C. and dried under vacuum. The temperature of the vials was kept at −20° C. during the initial stage (up to 22 hours) of drying. Under vacuum, the temperature was elevated to 20° C. and kept for 26 hours, and it was further elevated to 40° C. and kept for 20 hours to give a freeze-dried pharmaceutical preparation containing AM-833.

EXAMPLE 5

Five grams of powdered NFLX were dissolved in 50 ml of 1M lactic acid, and diluted with distilled water for injection to 100 ml. This solution was filtered through a membrane filter (pore size 0.22 µm), and each 2 ml of the filtrate was filled into clean and sterilized vials. These vials were cooled to −40° C. and dried under vacuum in a manner similar to that of Example 1 to give a freeze-dried pharmaceutical preparation containing NFLX.

EXAMPLE 6

Five grams of powdered NFLX were dissolved in 15 ml of 1N hydrochloric acid solution, and the pH was adjusted to 4.6 with 1M sodium hydroxide solution, and diluted with distilled water for injection to 100 ml. This solution was filtered through a membrane filter (pore size 0.22 µm), and each 2 ml of the filtrate was filled into clean and sterilized vials. These vials were cooled to −40° C. and dried under vacuum in a similar manner as Example 1 to give a freeze-dried pharmaceutical preparation containing NFLX.

EXAMPLE 7

Five grams of powdered NFLX and 10 grams of glucose were dissolved in 15 ml of 1N hydrochloric acid solution and the pH was adjusted to 5.5 with 1N sodium hydroxide solution, and diluted with distilled water for injection to 100 ml. This solution was filtered through a membrane filter (pore size 0.22 µm), and each 2 ml of the filtrate was filled into clean and sterilized vials. These vials were cooled to −40° C. and dried under vacuum in a manner similar to that of Example 1 to give a freeze-dried pharmaceutical preparation containing NFLX.

EXAMPLE 8

Five grams of powdered OFLX were dissolved in 25 ml of 1M lactic acid and diluted with distilled water for injection to 100 ml. This solution was filtered through a membrane filter (pore size 0.22 µm), and each 2 ml of the filtrate was filled into clean and sterilized vials. These vials were cooled to −40° C. and dried under vacuum in a manner similar to that of Example 1 to give a freeze-dried pharmaceutical preparation containing OFLX.

EXAMPLE 9

Five grams of CPFX were dissolved in 15 ml of 1N sodium hydroxide solution, and diluted with distilled water for injection to 100 ml. This solution was filtered through a membrane filter (pore size 0.22 μm), and each 2 ml of the filtrate was filled into clean and sterilized vials. These vials were cooled to −42° C. The temperature was elevated to −10° C., and kept for 2 hours. Then, it was cooled again to −40° C. and dried under vacuum. The temperature of the vials was kept at −20° C. during the initial stage (up to 21 hours) of drying. Subsequently, the temperature was elevated to 20° C. and kept for 65 hours under vacuum to give a freeze-dried pharmaceutical preparation containing CPFX.

EXAMPLE 10

Five grams of powdered CPFX were dissolved in 45 ml of 1N acetic acid solution, and diluted with a water for injection to 100 ml. This solution was filtered through a membrane filter (pore size 0.22 μm), and each 2 ml of the filtrate was filled into clean and sterilized vials. These vials were refrigerated by cooling to −42° C. and dried under vacuum in a manner similar to that of Example 9 to give a freeze-dried pharmaceutical preparation containing CPFX.

EXAMPLE 11

Five grams of powdered CPFX were dissolved in distilled water for injection and dissolved in 100 ml of distilled water. This solution was filtered through a membrane filter (pore size 0.22 μm), and each 2 ml of the filtrate was filled into clean and sterilized vials. These vials were cooled to −40° C. and dried under vacuum in a manner similar to that of Example 1 to give a freeze-dried pharmaceutical preparation containing CPFX.

EXAMPLE 12

Five grams of powdered ENX were dissolved in 25 ml of 1M lactic acid, the pH was adjusted to 4.5 with 1N sodium hydroxide solution, and diluted with distilled water for injection to 100 ml. This solution was filtered through a membrane filter (pore size 0.22 μm), and each 2 ml of the filtrate was filled into clean and sterilized vials. These vials were refrigerated by cooling to −40° C. and dried under vacuum in a manner similar to that of Example 1 to give a freeze-dried pharmaceutical preparation containing ENX.

EXAMPLE 13

Five grams of powdered AM-1091 were dissolved in distilled water for injection and diluted up to 100 ml with the distilled water. This solution was filtered through a membrane filter (pore size 0.22 μm), and each 2 ml of the filtrate was filled into clean and sterilized vials. These vials were cooled to −40° C. and dried under vacuum. The temperature of the vials was kept at −20° C. during the initial stage (up to 5 hours) of drying. Subsequently, the temperature was elevated to 20° C. and kept for 63 hours for drying under vacuum to give a freeze-dried pharmaceutical preparation containing AM-1091.

EXAMPLE 14

Five grams of powdered AM-1091 were dissolved in 25 ml of 1N sodium hydroxide solution, and diluted with distilled water for injection to 100 ml. This solution was filtered through a membrane filter (pore size 0.22 μm), and each 2 ml of the filtrate was filled into clean and sterilized vials. These vials were cooled to −40° C. The temperature was elevated to −10° C., and kept for 5 hours. Then, it was lowered again to −40° C. and dried under vacuum. The temperature of the vials was kept at −20° C. during the initial stage (up to 6 hours) of drying. Subsequently, the temperature was elevated to 20° C. and kept for 21 hours for drying under vacuum to give a freeze-dried pharmaceutical preparation containing AM-1091.

EXAMPLE 15

One gram of powdered NY-198 was dissolved in 20 ml of acetic acid and diluted with distilled water for injection to 50 ml. This solution was filtered through a membrane filter (pore size 0.22 μm), and each 2 ml of the filtrate was filled into clean and sterilized vials. These vials were cooled to −40° C. and dried under vacuum in a manner similar to that of Example 14 to give a freeze-dried pharmaceutical preparation containing NY-198.

EXAMPLE 16

One gram of powdered T-3262 was dissolved in 20 ml of 1M lactic acid and diluted with distilled water for injection to 50 ml. This solution was filtered through a membrane filter (pore size 0.22 μm), and each 2 ml of the filtrate was filled into clean and sterilized vials. These vials were cooled to −40° C. and dried under vacuum in a manner similar to that of Example 1 to give a freeze-dried pharmaceutical preparation containing T-3262.

STABILITY TEST

The freeze-dried pharmaceutical preparations obtained were evaluated by a stability test, under light (fluorescence lamp, 1,200,000 Lux-hours) and heat (50° C., 3 months) as compared with the solution prepared by using the same components.

The results are shown in Table 1. These freeze-dried pharmaceutical preparations of the present invention have excellent properties, particularly with respect to stability as compared with those for the solutions.

TABLE 1

Result of the Stability Tests of the Freeze-Dried Pharmaceutical Preparations of this Invention and Solutions

| Examples No. | Light (fluorescence lamp) | | Heat (50° C., 3 months) | |
|---|---|---|---|---|
| | Freeze-dried | Solution | Freeze-dried | Solution |
| 1 | no changes | yellowish | no changes | yellowish |
| 6 | no changes | slightly yellowish | no changes | no changes |
| 8 | no changes | slightly yellowish | no changes | no changes |
| 12 | no changes | slightly yellowish | no changes | no changes |
| 13 | no changes | precipitate of light brown | no changes | no changes |
| 15 | no changes | slightly brown | no changes | no changes |

What is claimed is:

1. A freeze-dried pharmaceutical preparation containing the compound of the following formula (I),

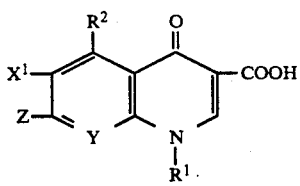

wherein $R^1$ represents a cycloalkyl group having 3 to 6 carbon atoms, straight or branched alkyl group having 1 to 3 carbon atoms, lower haloalkyl group, lower alkenyl group, lower hydroxyalkyl group, lower alkylamino group having 1 to 3 carbon atoms or phenyl group which may be substituted by fluorine atoms; $R^2$ represents a hydrogen atom, halogen atom, nitro group or amino group; $X^1$ represents a halogen atom; Y represents $CX^2$, (wherein $X^2$ represents a halogen atom, or lower alkyl or alkoxy group), Z represents

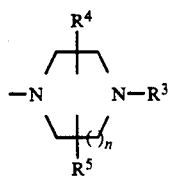

(wherein n is 1 or 2; $R^3$ represents a hydrogen atom or alkyl group having 1 or 3 carbon atoms, $R^4$ and $R^5$ each represent independently a hydrogen atom, alkyl group having 1 to 3 carbon atoms, lower aminoalkyl group, lower hydroxyalkyl group or phenyl group or

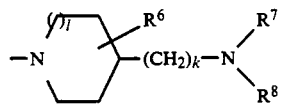

wherein k is 0 or 1, l is 0, 1 or 2, $R^6$ represents a hydrogen atom, halogen atom, alkyl group having 1 to 3 carbon atoms or hydroxy group, $R^7$ represents a hydrogen atom, alkyl group, having 1 to 3 carbon atoms, lower haloalkyl group or lower hydroxyalkyl group; $R^8$ represents a hydrogen atom or alkyl group having 1 to 3 carbon atoms; the hydrates or the pharmaceutically acceptable acid addition or alkali salts thereof.

2. The freeze-dried pharmaceutical preparation of claim 1 in which the compound is 6,8-difluoro-1-(2-fluoroethyl)-1,4-dihydro-7-(4-methyl-1-piperazinyl)-4-oxo-3-quinolinecarboxylic acid.

3. The freeze-dried pharmaceutical preparation of claim 1 in which the compound is 7-(3-amino-1-pyrrolidinyl)-8-chloro-1-cyclopropyl-6-fluoro-1,4-dihydro-4-oxo-3-quinolinecarboxylic acid.

4. The freeze-dried pharmaceutical preparation of claim 1 in which the compound is 1-ethyl-6,8-difluoro-1,4-dihydro-7-(3-methyl-1-piperazinyl)-4-oxo-3-quinolinecarboxylic acid.

5. A method for preparing the freeze-dried pharmaceutical preparation of claim 1 which comprises dissolving a compound having the formula 1 water containing an acid or alkali, then freeze-drying the solution.

6. The method of claim 5 wherein the acid is selected from the group consisting of hydrochloric acid, lactic acid and acetic acid.

7. The method of claim 5 wherein the alkali is selected from the group consisting of sodium hydroxide and potassium hydroxide.

8. The method of claim 5 wherein the concentration of compound I in the solution is from 0.1 to 30 w/v %.

9. The method of claim 8 wherein the concentration of compound I is from 5 to 15 w/v %.

10. The method of claim 5 wherein the solution is cooled to $-40°$ C. and then freeze-dried.

11. The freeze-dried composition of claim 1 containing an antibacterial effective amount of compound I.

12. A method for preparing a parenteral solution of an antibacterial agent comprising dissolving the composition of claim 1 in distilled water for injection.

13. A method for treating a patient for a bacterial infection comprising administering a therapeutically effective amount of a solution prepared by the method of claim 12.

* * * * *